United States Patent
Ibrahim et al.

(10) Patent No.: US 11,926,606 B1
(45) Date of Patent: Mar. 12, 2024

(54) **ISOLATION OF TOCOPHEROL FROM *COMMIPHORA MYRRHA***

(71) Applicant: KING FAISAL UNIVERSITY, Al-Ahsa (SA)

(72) Inventors: Amel Yousif Ahmed Ibrahim, Al-Ahsa (SA); Abdalla Ahmed Elbashir, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/232,448

(22) Filed: Aug. 10, 2023

(51) Int. Cl.
*C07D 311/74* (2006.01)
*B01D 3/00* (2006.01)
*C07D 311/72* (2006.01)

(52) U.S. Cl.
CPC ............ *C07D 311/74* (2013.01); *B01D 3/001* (2013.01); *C07D 311/72* (2013.01)

(58) Field of Classification Search
None
See application file for complete search history.

(56) References Cited

U.S. PATENT DOCUMENTS 10,512,603 B2   12/2019   AlmiÑana Domènech et al.

FOREIGN PATENT DOCUMENTS

EP   3130336 A1   2/2017

OTHER PUBLICATIONS

Mustafa, et al., Academicia Globe: Inderscience Research, 3:83. (Year: 2022).*
Khalil, et al., AMB Express, 10:1. (Year: 2020).*
Germano, A. et al., "A Pilot Study on Bioactive Constituents and Analgesic Effects of MyrLiq®, a Commiphora myrrha Extract with a High Furanodiene Content", BioMed Research International 2017:3804356 (2017).
Miralrio, A. et al., "Plant Extracts as Green Corrosion Inhibitors for Different Metal Surfaces and Corrosive Media: A Review", Processes 8:942 (2020).

* cited by examiner

*Primary Examiner* — Michael Barker
(74) *Attorney, Agent, or Firm* — Nath, Goldberg & Meyer; Richard C. Litman

(57) ABSTRACT

Methods of isolating tocopherol from *Commiphora myrrha* using a non-polar solvent are provided.

12 Claims, 1 Drawing Sheet

ISOLATION OF TOCOPHEROL FROM *COMMIPHORA MYRRHA*

BACKGROUND

1. Field

The disclosure of the present patent application relates to a method of isolating tocopherol from natural sources, and particularly to a method of isolating tocopherol from *Commiphora Myrrha*.

2. DESCRIPTION OF THE RELATED ART

Tocopherols are a class of organic compounds comprising various methylated phenols, many of which have vitamin E activity. Tocopherols belong to a class of phenolic antioxidants that can inhibit lipid autoxidation by scavenging free radicals and reacting with singlet oxygen. Tocopherols are classified into several types assigned as α, β, δ, and γ. They show powerful antioxidant activities, and act as an important sort of vitamin E. Of these varieties, α-Tocopherol is commonly used as a dietary supplement for patients with a deficiency of vitamin E. Based upon Tocopherols' antioxidant properties, they have been studied for their potential in treating or preventing a variety of diseases, including cardiovascular diseases [Mathur P. et al 2015] and cancer [Gupta S. et al 2016].

Generally, naturally sourced d-α-tocopherol can be extracted and purified from seed oils, or γ-tocopherol can be extracted, purified, and methylated to create d-alpha-tocopherol. However, industrial synthesis remains a significant source of the tocopherol used as supplements. In contrast to α-tocopherol extracted from plants, which also is called d-α-tocopherol, industrial synthesis creates dl-α-tocopherol. It is synthesized from a mixture of toluene and 2,3,5-trimethyl-hydroquinone that reacts with isophytol to all-rac-α-tocopherol, using iron in the presence of hydrogen chloride gas as a catalyst. The reaction mixture obtained is filtered and extracted with aqueous caustic soda. Toluene is removed by evaporation and the residue (all rac-α-tocopherol) is purified by vacuum distillation. This synthetic dl-α-tocopherol has approximately 50% of the potency of d-α-tocopherol.

Thus, a method of isolating tocopherol from natural sources solving the aforementioned problems is desired.

SUMMARY

In an embodiment, the present subject matter relates to a method of isolating tocopherol from *Commiphora myrrha*, which includes providing a sample of *Commiphora myrrha*, extracting the sample using a non-polar solvent, and distilling the extract to obtain tocopherol. In a non-limiting example, the sample of *Commiphora myrrha* may be a sample of *Commiphora myrrha* resin, the non-polar solvent may be hexane, and the extraction may be Soxhlet extraction.

These and other features of the present subject matter will become readily apparent upon further review of the following specification.

DETAILED DESCRIPTION OF THE PREFERRED EMBODIMENTS

Figure 1:
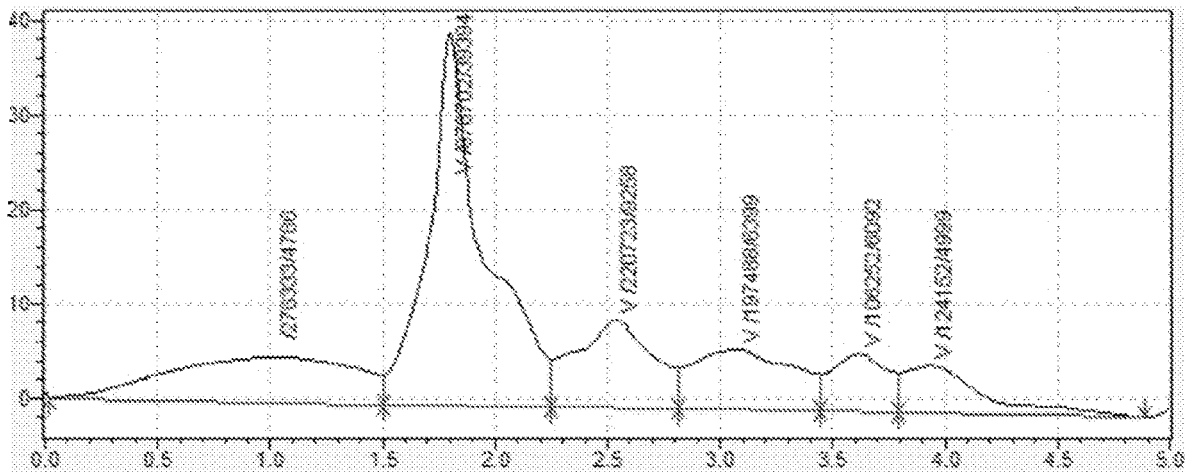
FIG. 1 depicts a chromatogram showing Tocopherols isolated from *Commiphora myrrha* resin.

The following definitions are provided for the purpose of understanding the present subject matter and for construing the appended patent claims.

Definitions

It should be understood that the drawings described above or below are for illustration purposes only. The drawings are not necessarily to scale, with emphasis generally being placed upon illustrating the principles of the present teachings. The drawings are not intended to limit the scope of the present teachings in any way.

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

It will be understood by those skilled in the art with respect to any chemical group containing one or more substituents that such groups are not intended to introduce any substitution or substitution patterns that are sterically impractical and/or physically non-feasible.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

The method of isolating tocopherol from *Commiphora myrrha* includes providing a sample of *Commiphora myrrha*, extracting the sample using a non-polar solvent, and distilling the extract to obtain tocopherol. In a non-limiting example, the sample of *Commiphora myrrha* may be a sample of *Commiphora myrrha* resin, the non-polar solvent may be hexane, and the extraction may be Soxhlet extraction.

Soxhlet extraction is a technique that is well known in the art and may be performed using any of the range of Soxhlet devices and methods that are well known to those of skill in the art. By way of non-limiting example, Soxhlet extraction may include the following general steps: the solvent is heated to reflux; the solvent vapour travels up a distillation arm, and floods into a chamber housing a thimble of solid; a condenser ensures that any solvent vapour cools and drips back down into the chamber housing the solid material; the chamber housing the solid material slowly fills with warm solvent; some of the desired compound dissolves in the warm solvent; when the Soxhlet chamber is almost full, the chamber is emptied by a siphon; the solvent is returned to the distillation flask; and a thimble ensures that the rapid motion of the solvent does not transport any solid material to the still pot. This cycle may be allowed to repeat many times, over hours or days. During each cycle, a portion of the non-volatile compound dissolves in the solvent. After many cycles the desired compound is concentrated in the distillation flask. One advantage of this system is that instead of many portions of warm solvent being passed through the sample, just one batch of solvent is recycled. After extraction the solvent is removed, typically by means of a rotary evaporator, yielding the extracted compound. The non-soluble portion of the extracted solid remains in the thimble and is usually discarded.

The solvent used in the method of isolating tocopherol from *Commiphora myrrha* may be any non-polar solvent. Examples of non-polar solvents for use in Soxhlet extraction are generally well-known to those of skill in the art, and may include but are not limited to pentane, iso-hexane, hexane, heptane, and octane. In one embodiment, the non-polar solvent may be hexane.

*Commiphora myrrha*, also known as called myrrh, African myrrh, herabol myrrh, Somali myrrhor, and common myrrh, is a tree in the Burseraceae family. It is one of the primary trees used in the production of myrrh, a resin made from dried tree sap. The tree is native to the Arabian peninsula and to Africa. *Commiphora myrrha* resin is produced when the plant's oleoresin oozes from incision in the bark and dries into small clumps of sap. This dried or hardened resin is harvested and used for a variety of purposes.

In an embodiment, the method of isolating tocopherol from *Commiphora myrrha* may include obtaining a sample of *Commiphora myrrha* resin, grinding the sample of *Commiphora myrrha* resin to obtain a *Commiphora myrrha* resin powder, extracting the *Commiphora myrrha* resin powder with a non-polar solvent to obtain an extract, and distilling the extract to obtain tocopherol. In some embodiments, about 0.5 to about 1.5 g of *Commiphora myrrha* may be extracted using about 0.050 ml to about 0.150 ml of the non-polar solvent. In a particular embodiment, about 1 g of *Commiphora myrrha* may be extracted using about 0.100 ml of a non-polar solvent. In another embodiment about 1 g of *Commiphora myrrha* resin powder may be extracted with about 0.100 ml hexane. The obtained tocopherol may have a concentration of about 18.97 mg/L.

In an embodiment, the method of isolating tocopherol from *Commiphora myrrha* may consist of obtaining a sample of *Commiphora myrrha* resin, grinding the sample of *Commiphora myrrha* resin to obtain a *Commiphora myrrha* resin powder, extracting the *Commiphora myrrha* resin powder with hexane to obtain an extract, and distilling the extract to obtain tocopherol. In some embodiments, about 0.5 to about 1.5 g of *Commiphora myrrha* may be extracted using about 0.050 ml to about 0.150 ml of the hexane. In a particular embodiment, about 1 g of *Commiphora myrrha* may be extracted using about 0.100 ml hexane. In another embodiment, about 1 g of *Commiphora myrrha* resin powder may be extracted with about 0.100 ml hexane. The obtained tocopherol may have a concentration of about 18.97 mg/L.

The present teachings may be better understood in view of the following examples.

EXAMPLE 1

Extraction of Tocopherol from *Commiphora myrrha* Resin

*Commiphora myrrha* resin samples were purchased from a local market in Al-Ahsa, Saudi Arabia. The samples were dried and ground to fine powder. About 1 g of *Commiphora myrrha* resin powder was weighed and placed into the thimble in a Soxhlet chamber and 0.100 ml of hexane was placed in a round bottom flask and assembled for Soxhlet extraction, then the distillation process was begun after completing the extraction. The final extract was filtered and placed into a polyethene container.

Three samples of Tocopherol were analyzed using High Liquid performance Chromatography (Prominence-i (LC-2030, LIQUID CHROMATOGRAPH)) from SHIMADZU with column C18 100 mm, UV detector and RF 20 detector, Sample injector A 1.5 mL and B 1.5 mL, Mobil phase containers normally A; Water and B; Methanol, 440 bar LC-2030 pump, Dual variable wavelength detector, Heater/Cooler oven and lab software solution consist of LC-2030 Controller, LC-2030 Auto sampler and LC-2030 Auto purge. The prepared samples as mentioned above were diluted in 10 ml sodium hydrogen phosphate buffer (NaHPO4) pH 3.5 and filtered over a 0.4 μm pore size syringe filter.

The mobile phase was prepared and consisted of 95%-NaHPO4 (0.025M) pH 4.5 and 5% Methanol (HPLC grade quality). 10 μL of each sample was injected. The samples were separated at 30° C. at a flow rate of 1.4 mL/min with a linear gradient at wavelength 290 nm.

Stock standard solutions of alpha Tocopherol (1000 μg/mL) were prepared by dissolving an appropriate amount directly in methanol and stored by keeping them protected from light and air at room temperature for a week. Working standard solutions were prepared daily.

Figure 2:
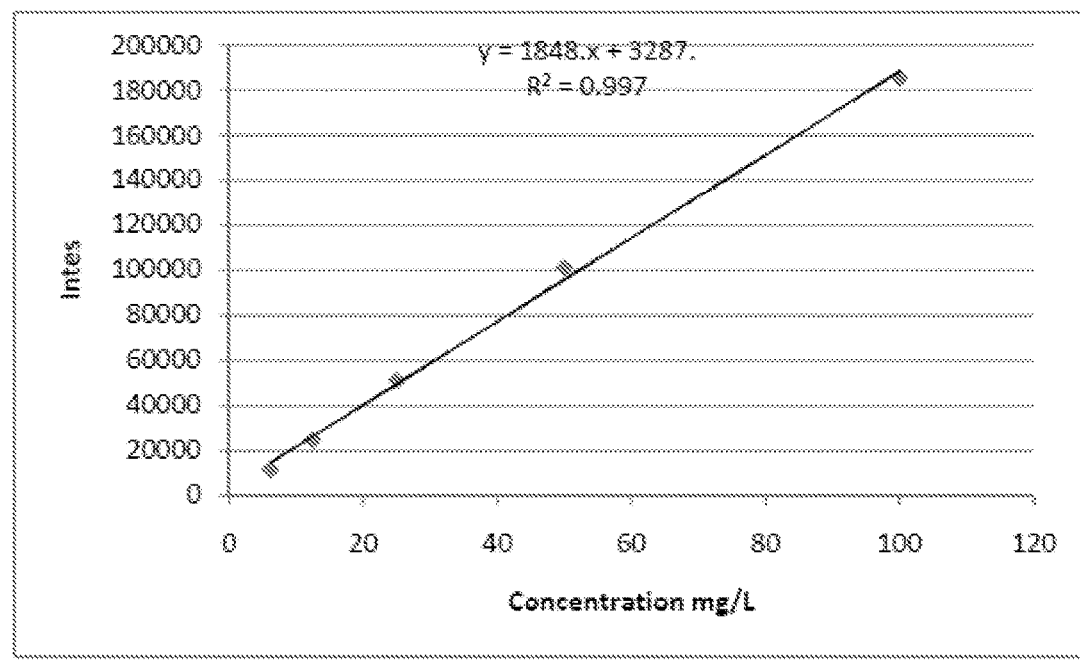
FIG. 2 depicts a graph showing a calibration curve for Tocopherol.

The stock standard solutions of alpha Tocopherol were used to produce the calibration curve shown in FIG. 2. This curve was used to calculate the concentration of Tocopherol present in the myrrha resin samples (See FIG. 1 for an example), which had a mean concentration of 18.97 mg/L (SD=0.150).

It is to be understood that the isolation of tocopherol from *Commiphora myrrha* is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of isolating tocopherol from *Commiphora myrrha* comprising:
    (a) providing a sample of *Commiphora myrrha*;
    (b) extracting the sample of *Commiphora myrrha* using a non-polar solvent to obtain an extract;
    (c) distilling the extract; and
    (d) isolating tocopherol.

2. The method of claim 1, wherein the extracting comprises Soxhlet extraction.

3. The method of claim 1, wherein the sample of *Commiphora myrrha* comprises *Commiphora myrrha* resin.

4. The method of claim 3, further comprising grinding the *Commiphora myrrha* resin to obtain a powder.

5. The method of claim 4, further comprising extracting about 0.5 to about 1.5 g of the powder with about 0.050 ml to about 0.150 ml of the non-polar solvent.

6. The method of claim 5, further comprising extracting about 1 g of the powder with about 0.100 ml of the non-polar solvent.

7. The method of claim 1, wherein the non-polar solvent is hexane.

8. The method of claim 1, wherein the concentration of the tocopherol is about 18.97 mg/L.

9. A method of isolating tocopherol from *Commiphora myrrha* consisting of:
    (a) providing a sample of *Commiphora myrrha* resin;
    (b) grinding the sample of *Commiphora myrrha* resin to obtain *Commiphora myrrha* resin powder;
    (b) extracting the *Commiphora myrrha* resin powder using hexane to obtain an extract; (c) distilling the extract; and
    (d) isolating tocopherol.

10. The method of claim 9 where the extracting comprises Soxhlet extraction.

11. The method of claim 9, wherein the concentration of the tocopherol is about 18.97 mg/L.

12. The method of claim 9, wherein about 1 g of the *Commiphora myrrha* resin powder is extracted with about 0.100 ml hexane.

\* \* \* \* \*